United States Patent [19]

Taylor

[11] 4,286,142
[45] Aug. 25, 1981

[54] ELECTRIC TUBE FURNACE

[75] Inventor: Raymond E. Taylor, West Lafayette, Ind.

[73] Assignee: Theta Industries, Inc., Port Washington, N.Y.

[21] Appl. No.: 87,015

[22] Filed: Oct. 22, 1979

[51] Int. Cl.³ .............................................. H05B 3/08
[52] U.S. Cl. .................... 219/390; 338/316; 13/25; 219/427
[58] Field of Search ............ 219/390, 427, 436, 553; 338/316; 13/25; 174/13, 99 E

[56] References Cited

U.S. PATENT DOCUMENTS

| 474,563 | 5/1892 | Moore | 174/13 |
|---|---|---|---|
| 744,387 | 11/1903 | O'Brien | 338/316 |
| 1,279,146 | 9/1918 | Peacock | 279/390 |
| 2,192,255 | 3/1940 | Bickley | 338/316 |
| 2,416,599 | 2/1947 | Victoreen | 338/316 |
| 2,768,277 | 10/1956 | Buck et al. | 279/390 |
| 2,896,060 | 7/1959 | Serfass et al. | 219/390 |
| 3,345,622 | 10/1967 | Matsushita | 338/316 |

FOREIGN PATENT DOCUMENTS

| 334522 | 3/1921 | Fed. Rep. of Germany | 338/316 |
|---|---|---|---|
| 1315187 | 12/1962 | France | 219/390 |

Primary Examiner—E. A. Goldberg
Assistant Examiner—Bernard Roskoski
Attorney, Agent, or Firm—Burton E. Levin

[57] ABSTRACT

An improved electric tube furnace is described in which a compressible leaf-spring attachment between the heating element tube and at least one of its supporting electric terminals compensates for linear thermal expansion of the tube without restricting access to the interior of the tube. The use of such furnace in an evacuated atmosphere for high temperature thermal diffusivity measurements is shown.

7 Claims, 4 Drawing Figures

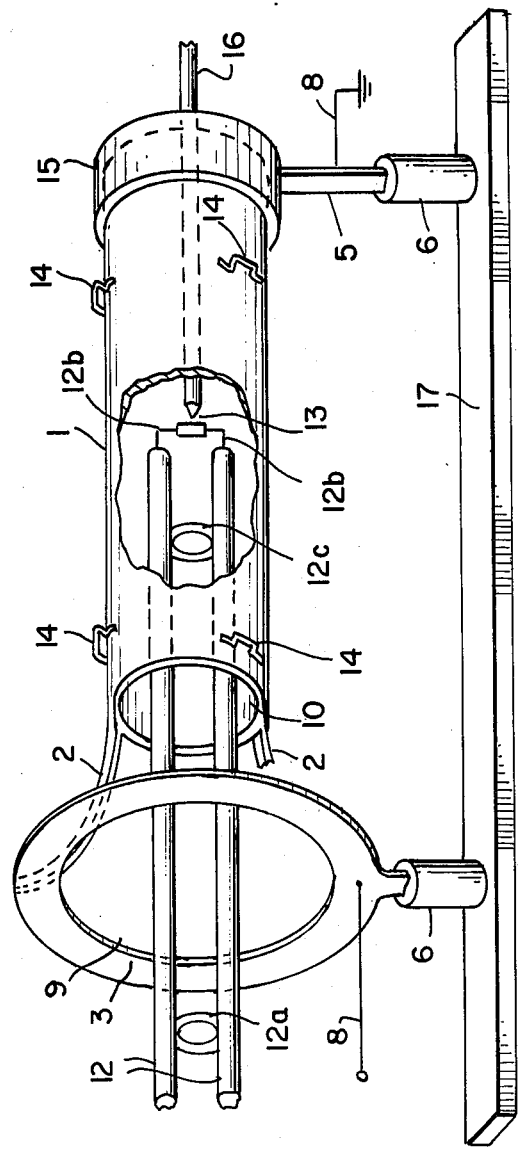
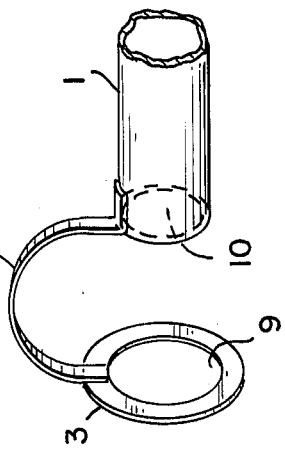
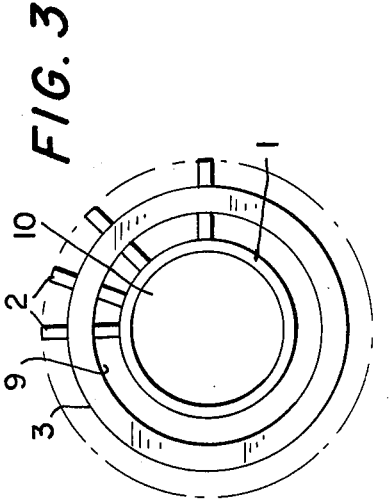
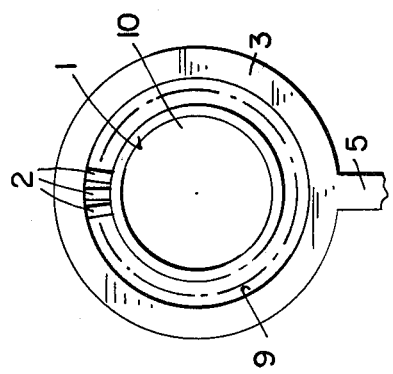

ELECTRIC TUBE FURNACE

BACKGROUND OF THE INVENTION

1. Field of the Invention

This invention relates generally to high temperature electric tube furnaces. More particularly, it relates to such furnaces in which the tubular heating element is rendered warp-resistant by a compressible metal attachment between the tube and at least one of its supporting electric terminals.

2. Description of the Prior Art

The electric tube furnace is well known. Basically it is a thin tubular metal heating element, which is firmly attached at its ends to electrodes and which is heated by its resistance to a high amperage current. Heating generally is concentrated in the tube by the use of electrodes that are massive relative to the tube and offer less resistance to the flow of electricity. The material to be heated simply is inserted into an open end of the tube. Such furnaces have been used for a wide variety of purposes, including the maintenance of specimens of materials at predetermined temperatures during measurement of their thermophysical properties.

One such property is thermal diffusivity, which can be measured by the flash method. Typically, this measurement involves bringing a small, disc-shape specimen to a uniform temperature by centering it within the tube of an electric tube furnace, subjecting the front face of the specimen to a short energy pulse from a solid state laser or flash lamp and measuring the resultant temperature rise on the rear face with a thermocouple or optical pyrometer. The diffusivity is calculated from the specimen thickness and the time required for the rear face temperature to reach a specific percentage of its maximum value. Since the energy pulse is on the order of one millisecond or less, the temperature rise on the rear face usually is well below 5° C. above the original specimen temperature and it is essential that one avoid distortions resulting from pre-energy pulse differences between the specimen and ambient temperatures. Ambient temperature control, and maintenance of that temperature uniformly over the specimen, is particularly critical at very high temperatures, such as those which often are required to measure thermal diffusivity near the phase transition temperature of the specimen material. Such near-phase transition temperatures often are in excess of 1000° C. and may be as high as 3000° C. or higher.

When the thermal diffusivity specimen and the tube of the electric tube furnace are resistant to oxidation and the maximum temperature does not exceed about 800° C. to 1000° C., both specimen heating and diffusivity measurement often may be done in the atmosphere. While bringing the tube up to the desired temperature for such atmospheric measurement, it is possible occasionally to reposition the electrodes which are firmly attached to the tube, so as to relieve the compressive force on the tube resulting from its linear thermal expansion. At higher temperatures oxidation of the specimen and furnace must be avoided by enclosing them in an oxygen poor zone, such as under an evacuated bell jar.

The presence of such jar makes it nearly impossible to manipulate its contents. Thus, as heating proceeds, the electrodes cannot be repositioned to accomodate the linear thermal expansion of the tubular heating element, and warping of the tube may occur. This effect becomes increasingly severe as the temperature is increased, and at temperatures from about 1600° C. to about 3000° C. or higher, non-uniform heating of the specimen (with accompanying erratic thermal diffusivity measurement,) may result from the fact that the walls of the warped tube are not equidistant from the specimen. In extreme cases, permanent damage may be done to the fragile tube. Similar problems often are experienced with prior art tube furnaces which are used for a wide variety of other purposes.

SUMMARY OF THE INVENTION

It is an object of this invention to provide an electrically heated tube furnace which does not warp when subjected to high temperatures. A further object of this invention is to provide such furnace in which the tubular metal heating element is attached at each end to an electrode, at least one such attachment being through flexible metal conductors which, by bending, compensate for the linear thermal expansion of the tube. It is a specific object of this invention to provide such warp-resistant electric tube furnace which is particularly well suited for use in an inaccesible location, such as under the evacuated bell-jar of a high temperature thermal diffusivity measuring apparatus.

It has been found that these objects and other advantages, which will be apparent from this specification, are achieved by the invention described below.

Broadly, my invention is a warp resistant high temperature electric tube furnace comprising a rigid heating element tube having open ends and a supporting electric terminal ring coaxially disposed and attached adjacent to each end of said tube, at least one said ring being compressibly attached to said tube through a plurality of flexible metal connectors. The presence of such compressible attachment relieves the pressure on the fragile tube which otherwise would result from its linear thermal expansion and minimizes the possibility of tube warping.

A more specific embodiment of my invention is such furnace in which the electrical resistance of the tube is higher than that of each of the rings and at least as high as the total electrical resistance of the connectors attached to each such ring, thereby concentrating the heating effect within the tube. Another specific embodiment of my invention is such electric tube furnace in which the terminal ring openings are at least as large as the inside diameter of the tube and the connectors radiate from the periphery of the tube to the ring, thereby providing unrestricted access to the open ends of the tube.

BRIEF DESCRIPTION OF THE DRAWINGS

FIG. 1 is a schematic perspective view of an embodiment of the electric tube furnace of this invention in which the flexible metal connectors (only one shown) are linear extensions of the wall of the tube which are curved away from the axis of the tube. The tube is partially cut away to show the use of the furnace for the measurement of thermal diffusivity.

FIG. 2 is a partial plan view of the left end of the furnace of FIG. 1 showing the disposition of the flexible connectors between the ring terminal and the tube.

FIG. 3 is a similar partial plan view of the end of another furnace of this invention showing an alternate disposition of the flexible metal connectors between the ring terminal and the tube.

FIG. 4 is a partial perspective view of the furnace of FIG. 3 showing details of the attachment of a single connector to the terminal ring and the tube.

DESCRIPTION OF THE PREFERRED EMBODIMENTS

The heating element used in the furnace of this invention is an open ended tube which functions as an electric resistance heater and which may be construed of any electric conductor which does not appreciably soften or melt at the desired temperature of use. Suitable conductors include the metals nichel, chromium, iron, osmium, iridium, tantalum and tungsten. For very high temperatures, for example 1600° to 2600° C., tantalum and tungsten are preferred metals of construction. At extremely high temperatures of about 2600° to about 3300° C., tungsten is especially preferred. The length and inside diameter of the tube may be varied widely depending upon the size and shape of the object that is to be inserted into it and heated. The wall thickness, ideally, is as thin as possible, consistent with the requirement that the tube remain rigin in use; that is, that when heated it does not sag between points of support or otherwise become distorted by compression forces resulting from thermal expansion.

The tube is supported by electric terminal rings which are coaxially disposed at or near its ends and which, advantageously, are firmly fixed to a sturdy base. Additional intermediate electrically non-conducting supports may be useful with extremely long or thin walled tubes. The terminal rings also may be made of any solid metal and, preferably, exhibit electrical resistance that is significantly lower than that of the tube so as to concentrate electrical heating in the tube. This usually can be accomplished by using copper alloy terminal rings which are massive relative to the tube. Massive construction of the terminal rings also serves to dissipate any heat absorbed by radiation from the tube. It often is desirable to further dissipate this absorbed heat by providing a passage through the terminal rings for the circulation of a cooling fluid. In order to provide unrestricted access to the interior of the tube it is preferred that the ring opening be at least as large as the inside diameter of the tube.

To compensate for linear thermal expansion of the tube, flexible metal connectors are employed between at least one of the ring terminals and the adjacent end of the tube. Since these connectors are subject to both conductive and radiant heating from the tube and are not susceptible to fluid cooling, it is essential that they be made of a material which does not lose appreciable strength at high temperatures. For very high temperature operation, tungsten and tantalum are preferred. It also is preferred that the total electrical resistance of the connectors attached to each terminal be no greater, and more preferably less, than that of the tube in order to concentrate electrical heating in the tube. Such equal or lower electrical resistance can be achieved readily by coupling a tube with connectors made of a different metal that is a better electrical conductor or, when tube and connector metals are the same, by coupling that tube with connectors having an equal or larger total electrical cross-section. When the total electrical resistance of such connectors is significantly less than that of the tube, it often is possible to employ steel or other relatively low melting metal connectors, even when the designed maximum temperature of the furnace requires a tungsten or tantalum tube.

The use of flexible metal connectors as the means of attachment between a terminal ring and the adjacent end of the tube provides a firmly supporting attachment that securely holds the tube end, and, being compressible, compensates for linear thermal expansion of the tube without the necessity of repositioning the ring. Although a wide variety of connector shapes is possible (for example, a multiplicity of loose wire or coil spring connectors), it has been found that lateral and rotational movement of the tube end is minimized by the use of flat rectangular metal strip connectors which are symmetrically disposed about, and radiate from the periphery of the tube to the ring, thereby functioning as leaf-springs. In order to minimize compressive forces on the tube, these strips preferably are curved or bent. It is especially preferred that these strips contain at least one curve or bend away from the axis of the tube and that no portion thereof restrict access to the interior of the tube.

Such strips may be integral laterial extensions of the tube walls (as in FIG. 1) or may be separate elements which are attached to the tube wall either directly or through a suitable conductive collar.

Electrical heating of the furnace is effected by imposing a suitably high amperage electric current across the terminals.

Referring again to FIG. 1, there is illustrated an embodiment of this invention which, as shown, is particularly well suited for high temperature thermal diffusivity measurements. Tantalum heating element tube 1 is attached to and supported at one end by a massive copper terminal ring 15 which is attached through copper post 5 to a grounded electrical connection 8. Post 5 is securely held to base 17 through insulator 6. The other end of tube 1 is attached to massive copper terminal ring 3 through flat rectangular tantalum connector strips 2 (only one complete strip shown). As shown here and in FIG. 2, these strips are symmetrically disposed extensions of the wall of tube 1 which are bent outward from the axis of the tube to terminal ring 3. Terminal ring 3 is held firmly through insulator 6 to base 17 and has an electrical connection 8 to a source of high amperage current. As shown here, tube 1 has supports 14 for an encircling tubular radiation shield (not shown).

When this furnace is used for thermal diffusivity measurement, a specimen 13 is introduced into the interior of the tube 1 through tube opening 10 and terminal ring opening 9. As shown here, specimen 13 is supported by specimen holder 12b, which in turn is attached to rods 12. Uniform spacing of rods 12 is accomplished by rings 12a. For high temperature usage, the entire furnace, the specimen, and the specimen supporting elements are enclosed within an evacuated bell-jar (not shown). When the specimen has reached the desired temperature, a flash of high energy is impinged on one surface of the specimen 13 through the openings in spacing rings 12a. The change in temperature on the other side of the specimen is measured by thermocouple 16.

As noted above, FIG. 2 shows the symmetrical disposition of the linear extensions 2 of tube 1 which flare out to terminal ring 3. Linear thermal expansion of the tube is compensated by further bending of connectors 2, thereby relieving the compression forces which otherwise would be imposed on the tube.

FIG. 3 shows the disposition of another type of flexible metal connector, a "U" shaped leaf spring which is outstanding for imparting lateral stability to the end of the tube, thereby maintaining the coaxial relationship of the tube and ring even at extremely high temperatures. Flat rectangular metal strips 2 bow outward from the end of tube 1 to ring 3, thereby permitting unrestricted access to opening 10 in the tube through opening 9 in the terminal ring.

FIG. 4 more clearly illustrates the shape of one such bowed metal connector 2 of FIG. 3 which, as shown, is attached to but not integral with the walls of tube 1.

It will, of course, be understood that various additions and modifications may be made in the embodiments of this invention described above without departing from the spirit and scope of the invention as defined in the claims below.

The embodiments of the invention in which an exclusive property or privilege is claimed are defined as follows:

1. Warp resistant high temperature electric tube furnace comprising a rigid metal heating element tube having open ends and a supporting electric terminal ring coaxially disposed and attached adjacent to each end of said tube, each said ring having an inside diameter at least as large as the inside diameter of said tube and at least one said ring being tandemly spaced from said tube and remotely, compressibly attached through a plurality of flexible elongated rectangular metal strip connectors which are symmetrically spaced about the periphery of said tube and radiate to said remotely attached ring.

2. Furnace of claim 1 wherein the electrical resistance of said tube is higher than that of each said ring and at least as high as the total electrical resistance of the connectors attached to said remotely attached ring.

3. Furnace of claim 2 wherein each of said connectors and said tube is made of a metal selected from the group consisting of tantalum and tungsten.

4. Furnace of claim 2 wherein said strips of metal are linear extensions of the wall of said tube which curve away from the axis of said tube to said remotely attached ring.

5. Furnace of claim 4 wherein the inside diameter of said remotely attached ring is larger than the inside diameter of said tube.

6. Furnace of claim 3 wherein said strips of metal connecting said tube to said remotely attached ring are bowed away from the axis of said tube.

7. Furnace of claim 6 wherein said bowed strips are "U" shape leaf springs.

* * * * *